United States Patent [19]

Rüger et al.

[11] Patent Number: 5,264,432
[45] Date of Patent: Nov. 23, 1993

[54] 5-(1-AMINOACYL)-5,10-DIHYDRO-11H-DIBENZO[B,E](1,4)DIAZEPIN-11-ONES

[75] Inventors: Carla Rüger, Radebeul; Wolfgang Sauer, Dresden; Dieter Lohmann, Radebeul; Hildegard Poppe; Reni Bartsch, both of Dresden, all of German Democratic Rep.; Arkadij M. Lichoserstov, Moscow, U.S.S.R.; Natalja V. Kaverina, Moscow, U.S.S.R.; Alexandr P. Skoldinov, Moscow, U.S.S.R.; Yekaterina K. Grigoryeva, Moscow, U.S.S.R.; Yekaterina A. Talmachova, Moscow, U.S.S.R.; Valentin V. Lyskovzev, Moscow, U.S.S.R.; Alwina W. Stawrowskaya, Moscow, U.S.S.R.; Gennadi G. Chichkanov, Moscow, U.S.S.R.

[73] Assignee: Arzneimittelwerk Dresden G.m.b.H, Radebeul, German Democratic Rep.

[21] Appl. No.: 971,671

[22] Filed: Nov. 4, 1992

Related U.S. Application Data

[63] Continuation of Ser. No. 559,309, Jul. 30, 1990, abandoned.

[30] Foreign Application Priority Data

Jul. 31, 1989 [DD] German Democratic Rep. ..................... 3312797

[51] Int. Cl.$^5$ .................... A61K 31/55; C07D 243/38
[52] U.S. Cl. ..................... 514/220; 540/495
[58] Field of Search ................ 540/495; 514/220

[56] References Cited

U.S. PATENT DOCUMENTS

| | | | |
|---|---|---|---|
| 4,210,648 | 7/1980 | Schmidt | 540/495 |
| 4,213,985 | 7/1980 | Schmidt | 540/495 |
| 4,317,823 | 3/1982 | Rainer | 540/495 |
| 4,381,301 | 4/1983 | Rainer | 540/495 |
| 4,556,653 | 12/1985 | Giani | 514/220 |
| 4,749,788 | 6/1988 | Lo et al. | 540/495 |

FOREIGN PATENT DOCUMENTS

| | | | |
|---|---|---|---|
| 309422 | 3/1989 | European Pat. Off. | 540/495 |
| 236731 | 6/1986 | Fed. Rep. of Germany . | |

OTHER PUBLICATIONS

"Textbook of Anatomy and Physiology" (Anthony et al., ed.) 8th Edition, p. 231 (1971).

*Primary Examiner*—Mark L. Berch
*Attorney, Agent, or Firm*—Schweitzer, Cornman & Gross

[57] ABSTRACT 5-(w-Aminoacyl)-5,10-dihydro-11H-dibenzo(b,e)(1,4)-diazepine-11-ones, and their preparation are disclosed for treatment of antiarrhythmia and as an anticholinergic drug.

3 Claims, No Drawings

5-(1-AMINOACYL)-5,10-DIHYDRO-11H-DIBENZO[B,E](1,4)DIAZEPIN-11-ONES

This is a continuing application of U.S. Ser. No. 559,309, filed on Jul. 30, 1990, now abandoned.

FIELD OF INVENTION

The present invention relates to new 5-(-aminoacyl)-5,10-dihydro-11H-dibenzo(b,e)(1,4)-diazepine-11-ones

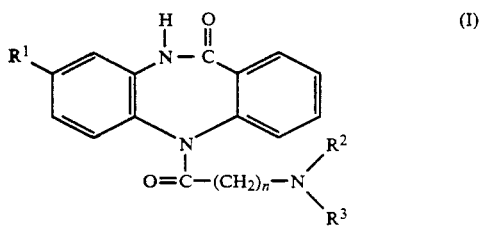

and their pharmaceutically acceptable acid addition salts, to method for making, to pharmaceutical preparations containing these compounds, and to their pharmaceutical use particularly for the treatment of arrhythmia and cholinergic disorders.

BACKGROUND OF THE INVENTION 5,10-Dihydro-11H-dibenzo(b,e)(1,4)-diazepine-11-ones with an aminoacetyl or an aminopropionyl group in the 5 position, are already known e.g. from German accepted patent application Nos. 1,936,670; 2,022,790; 2,065,570, German published application 1,795,176; 1,931,487; 3,028,001; 3,204,157; 3,204,158, Belgium patent No. 753,664; East German patent No. 236,731; and European patent publication No. 44,989. These new compounds have an antiulcerative and antisecretory effect.

Further 5,10-dihydro-11H-dibenzo(b,e)(1,4)-diazepine-11-ones, substituted in the 5 position with an aminoacetyl or aminopropionyl group, were described by A. M. Monro et al. in J. Med. Chem. 6, 255. However, their pharmacological properties were not given.

Moreover, 5,11-dihydro-6H-pyrido(2,3-b)(1,4)-benzodiazepine-6-ones, which have an effect on the heart rate, are known from e.g. German published patent applications Nos. 3,409,237; 3,523,002.

Most of the antiarrhythmic drugs of class I, such as lidocaine, ethmozine or propafenone have the property of lowering the heart rate in addition to their known antiarrhythmic effect. They are therefore suitable for the treatment of tachyarrhythmia.

For arrhythmias with a low pulse rate (bradyarrhythmias), these materials can therefore be used only in conjunction with atropine, so that a further lowering of the heart rate is prevented.

Agents, which have an antiarrhythmic as well as an anticholinergic effect and thus can be used for the treatment of bradyarrhythmias, are available only to a limited extent and have the disadvantage that they have predominantly an anticholinergic effect (atropine, ipratropium bromide) or predominantly an antiarrhythmic effect (quinidine, disopyramide).

There is therefore a need to find drugs, which have as balanced a ratio of antiarrhythmic to anticholinergic effect as possible and are thus suitable for the treatment of bradyarrhythmias (arrhythmias with a low pulse rate).

DESCRIPTION THE INVENTION

By the present invention, it is possible to synthesize new 5-(w-aminoacyl)-5,10-dihydro-11H-dibenzo(b,e)(1,4)-diazepine-11-ones of formula (I), and to their acid addition salts.

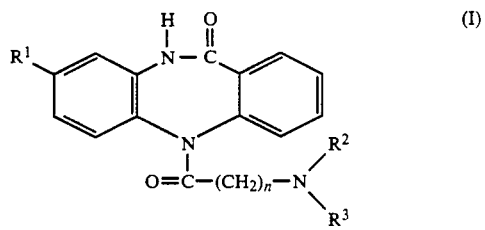

The compounds of formula (I) are highly effective cardiovascular drugs, which have a pronounced, strong antiarrhythmic effect and can therefore be used for the therapy of disordered actions of the heart.

While most antiarrhythmic drugs, such as lidocaine and quinidine, lower the cardiac rhythm, the compounds of formula (I), because of the anticholinergic property that is present at the same time, maintain the existing cardiac rhythm at the same level over a prolonged period.

As used throughout the specification and the claims the term "cholinergically induced disease" means a parasympathetic or sympathetic arrhythmic disturbance, such as tachyarrhythmia, and bradyarrhytmia.

The combination of antiarrhythmic and anticholinergic effect in compounds of formula (I) is very useful for the synthesis of drugs, which are to be used for the treatment of bradycardic rhythm disorders. In animal experiments, the strength of action of the compounds exceeds that of quinidine and lidocaine.

It is an object of the present invention to find and provide new 5-(w-aminoacyl)-5,10-dihydro-11H-dibenzo(b,e)(1,4)-diazepine-11-ones of formula (I),

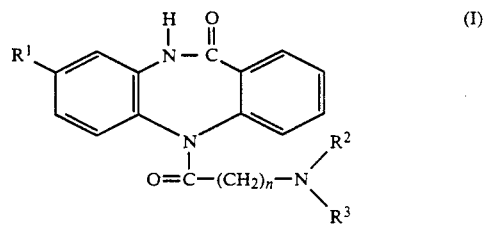

wherein
$R^1$ is hydrogen or chlorine;
$R^2$ is hydrogen
$R^3$ can be the same or different and are $C_{1-3}$ alkyl moieties, or together with the nitrogen atom to which they are linked are a morpholino, or N-methylpiperazino residue; and
n is a cardinal number of from 3 to 6;
with the proviso that when $R^2$ is hydrogen, $R^3$ can also be acyclohexyl residue; and their pharmaceutically acceptable acid addition salts and to pharmaceutical compositions containing these compounds, method for making, and to their pharmaceutical use.

Pursuant to the present invention, the compound of formula (I) prepared by
(a) a 5,10-dihydro-5-(w-halogenacyl)-11H-dibenzo(b,e)(1,4)-diazepine-11-one of formula (II)

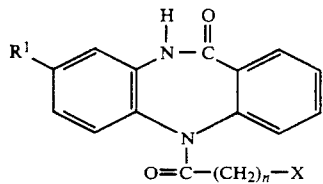

wherein R¹ and n have the same meaning as above, and X is a halogen atom, with an amine of formula (III)

in which R² and R³ have the same meaning as above, or with a salt of this amine, or (b) a 5,10-dihydro-11H-dibenzo(b,e)(1,4)-diazepine-11-one of formula (IV),

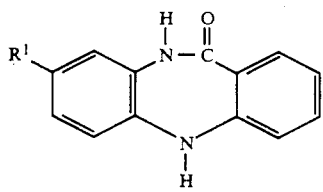

wherein R¹ has the meaning given above, with an aminoacyl halide of formula (V),

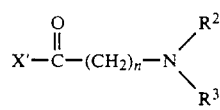

wherein R², R³ and n have the same meaning given above and X' is a halogen atom, suitably chlorine or bromine, or with a salt of the aminoacyl halide.

The compounds obtained, having the formula (I), can be optionally converted to a pharmaceutically acceptable acid addition salt, or the base can be optionally released from the salt obtained from a compound of formula (I).

A particularly suitable embodiment of the invention is a 5-(w-aminoacyl)-5,10-dihydro-11H-dibenzo(b,e)(1,4)-diazepine-11-one of formula (VII)

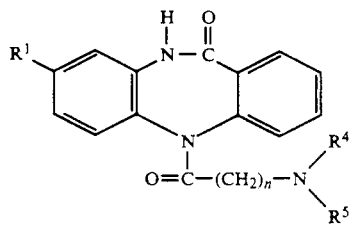

wherein
R¹ is hydrogen or chlorine,
R⁴ and R⁵, which can be the same or different, is each a $C_{1-3}$ alkyl residue or together with the nitrogen atom, to which they are linked, is a morpholino or N-methylpiperazino residue, and n is a cardinal number of from 3 to 6, and their pharmaceutically acceptable acid addition salt.

The compounds of formula (VII) can be synthesed by
(a) reacting a 5,10-dihydro-5-(w-halogenacyl)-11H-dibenzo(b,e)(1,4)-diazepine-11-one of formula II, wherein R¹ and n have the same meanings as above, and X is halogen, with an amine, of formula (VIII)

in which R⁴ and R⁵ have the same meaning as above, or with a salt of this amine, or by
(b) reacting a 5,10-dihydro-11H-dibenzo(b,e)(1,4)-diazepine-11-one of formula (IV), wherein R¹ has the same meaning as above, with an aminoacyl halide of formula (IX)

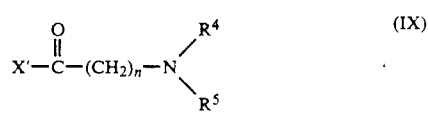

wherein R⁴ and R⁵ have the same meaning as above, and X' is a halogen, suitably chlorine or bromine, or with a salt of this aminoacyl halide,
and the compounds obtained have formula (VII) and can be optionally converted with pharmaceutically acceptable inorganic or organic acids into their acid addition salts, or the bases can be optionally released from the salts obtained of the compounds of formula (VII).

A further, suitable embodiment of the invention is a 5-(w-aminoacyl)-5,10-dihydro-11H-dibenzo(b,e)(1,4)-diazepine-11-ones of formula (X)

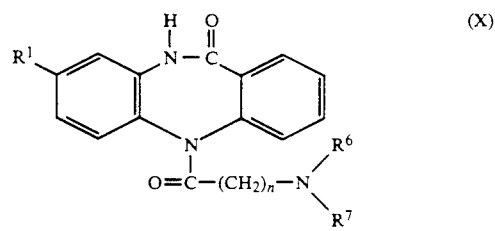

wherein
R¹ is hydrogen or chlorine,
R⁶ is hydrogen,
R⁷ is a $C_{1-3}$ alkyl residue or a cyclohexyl residue, and n is a cardinal number of from 3 to 6
and their pharmaceutically acceptable acid addition salts.

The compounds of formula (X) can be prepared by
(a) reacting a 5,10-dihydro-5-(1-halogenacyl)-11H-dibenzo(b,e)(1,4)-diazepine-11-one of formula (II), wherein R¹ and n have the same meaning as above, and X is halogen atom, with an amine of formula (XI)

in which R⁶ and R⁷ have the same meaning as above, or with a salt of this amine, or (b) reacting a 5,10-dihydro-11H-dibenzo(b,e)(1,4)-diazepine-11-one of formula (IV), wherein $R^1$ has the same meaning as above, with an aminoacyl halide of formula (XII)

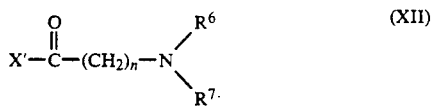

wherein $R^6$, $R^7$ and n have the same meaning as above, and X' is a halogen atom, preferably chlorine or bromine, or with a salt of this aminoacyl halide and the compounds obtained, having formula (X), can be optionally converted with pharmaceutically acceptable inorganic or organic acids into their corresponding acid addition salts or the bases can be optionally released from the salts of the compounds of formula (X).

A suitable embodiment of the invention can be synthesised of the compounds of formulae (I), (VII) and (X) in an inert organic solvent. Alcohols, such as ethanol, n-propanol or isopropanol, ethers such as dioxane or tetrahydrofuran, aromatic hydrocarbons such as benzene, toluene or xylene, halogenated aliphatic or aromatic hydrocarbons, such as chloroform, 1,2-dichloroethane, carbon tetrachloride or chlorobenzene or dipolar, aprotic solvents, such as dimethylformamide, acetonitrile or dimethyl sulfoxide are suitable for this purpose as inert organic solvents.

Another suitable embodiment of the invention can be prepared wherein an excess of a compound of formulae (III), (VIII) or (XI) is used as solvent.

The temperature for the synthesis of the compounds of formulae (I), (VII) and (X) can vary within wide limits. In a particularly suitable embodiment of the invention, the synthesis is carried out at a temperatures between about room temperature and about 150° C.

In accordancwe with the present invention, the synthesis of compounds of formulae (I), (VII) and (X) can be carried out in the presence of an acid acceptor. Alkali carbonates, alkali hydrogen carbonates, or tertiary organic amines, such as triethylamine, pyridine or N,N,-dimethylaniline, for example, are suitable as acid acceptors.

The compounds obtained having formulae (I), (VII) and (X) can be converted into their pharmaceutically acceptable acid addition salts in a mannre known perse.

Examples of such pharmaceutically acceptable acids are hydrochloric acid, hydrobromic acid, hydriodic acid, sulfuric acid, phosphoric acid, acetic acid, tartaric acid, citric acid, fumaric acid, maleic acid, succinic acid or ascorbic acid.

The present invention further comprises pharmaceutical compositions containing at least one compound of formulae (I), (VII) or (X), or their pharmaceutically acceptable acid addition salts.

Compounds of the present invention are useful as actives in pharmaceutical compositions for the treatment of arrhythmias, particularly bradyarrhythmias, containing at least one compound of formulae (I), (VII) or (X), or their pharmaceutically acceptable acid addition salts.

Compounds of formulae (I), (VII) and (X) or their pharmaceutically acceptable acid addition salts, are also useful as anticholinergics.

Preparations containing as an active, one or more compounds of the present invention can be provided in any desirable dosage forms, such as tablets, sugar-coated pills, capsules, solutions, ampules or suppositories containing at least one compound of formulae (I), (VII) and (X), or their pharmaceutically acceptable acid addition salts, optionally in admixture with inert, pharmaceutically suitable carriers and/or adjuvants. They can be prepared by methods, which are generally known per se and are customary in pharmaceutical practice.

The 5,10-dihydro-11H-dibenzo(b,e)(1,4)-diazepine-11-ones of formula (IV), used as starting compounds herein are known compounds.

The starting compounds of formula (II), can be synthesized by methods similar to those known from the literature, by the reacting a 5,10-dihydro-11H-dibenzo(b,e)(1,4)-diazepine-11-one of formula (IV), wherein $R^1$ has the meaning given above, with a halogenacyl halide of formula (VI)

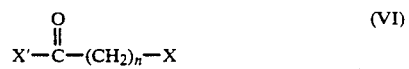

wherein X, X' and n have the same meaning as above, optionally in the presence of a hydrogen halide-binding agent, such as an alkali carbonates, or an alkali hydrogen carbonate.

The reaction is suitably carried out in an inert organic solvent at an elevated temperature. As solvents, aromatic hydrocarbons, such as benzene, toluene or xylene, halogenated aromatic hydrocarbons such as chlorobenzene, but also esters such as ethyl acetate, can be used.

In animal trials, the new 5-(w-aminoacyl)-5,10-dihydro-11H-dibenzo(b,e)(1,4)-diazepine-11-ones of formulae (I), (VII) and (X) showed a pronounced antiarrhythmic effect. In various pharmacological models for testing the antiarrhythmic effectiveness, the inventive compounds proved to be significantly more effective than lidocaine and quinidine.

For example, it was possible to demonstrate on the $CaCl_2$ arrhythmia of the rat (this method is described by K. Femmer et al. in Pharmazie 40, page 836 (1985)) an antifibrillatory effect, which is distinctly greater than that of the comparison preparations, lidocaine and quinidine (see Table 1).

The compounds of formulae (I), (VII) and (X), when administered intravenously to rats, were found to be tolerated better than are the reference preparations.

Because of the increased potency of action and the better tolerance of the compounds of formulae (I), (VII) and (X), there is a significant increase in the therapeutic breadth (see Table 1, $Q=LD_{50}/ED_{50}$).

Since all previously used antiarrhythmic drugs have only a slight therapeutic breadth, a clear advantage, from the new compounds of the invention, can be expected also in this respect for the more reliable medicinal application for the treatment of other disorders.

Using the two-step coronary ligature on the dog according to Harris (by the method described by Kaverina et al. in Pharmazie 40, page 845 (1985)) as a model, the compounds of formulae (I), (VII) and (X) show a strong and long-lasting effect (see Tables 2 and 3).

It is remarkable that in contrast to other antiarrhythmic drugs such as lidocaine which possess no anticholinergic effect, and quinidine (Mokler, C. M. and C. G. Arman, J. Pharmacol. Exp. Ther., 136, page 114 (1962), [1]) which possesses an anticholinergic effect, which lead in this model to a decrease in the total number of heart contractions and a decrease in the ectopic arrhythmia, the new compounds leave the total number of heart contractions unaffected, while at the same time they lower the ectopy rate.

Already in the 5th minute after the intravenous injection of the compounds of formulae (I), (VII) and (X) at a concentration of 0.005 mmoles/kg (about 2.0 mg/kg) the ectopic arrhythmia is suppressed by a factor of 2 to 3 of the base value, while the total number of heart contractions remains constant. The effect on the ectopic arrhythmia lasts for 30 to 60 minutes.

regression analysis with a confidence interval of $p=0.05$ (values in parentheses).

Q is the ratio of $LD_{50\ iv.}/ED_{50\ iv.}$ to determine therapeutic breadth range.

Eff. Dose is the effective dose in mg/kg, as well as the duration of action in minutes in dogs, 24 hours after a two-step coronary ligature.

In Tables 2 and 3:

$\bar{x}$ is the average value s is standard deviation

The invention is further illustrated through the following examples:

TABLE 1

Antifibrillatory effect on the $CaCl_2$ arrhythmia of the rat, the coronary ligature on the dog, as well as orientating acute toxicity of the rat, in comparison with standard preparations.

| Compound | $CaCl_2$ arrhythmia of the rat, $ED_{50}$ (mg/kg) | acute toxicity of the rat $LD_{50}$ i.v., (mg/kg) | Q $LD_{50}/ED_{50}$ | harris dog effective dose (mg/kg) i.v. | effective action in minutes |
|---|---|---|---|---|---|
| Example 1 | 0.41 (0.22–0.78) | 85 (81–90) | 207 | 1.76 | 60 |
| Example 4 | 0.044 (0.016–0.12) | 71 (62–81) | 1614 | 1.93 | 30 |
| Example 6 | 0.44 (0.15–0.76) | 38 (32–45) | 86 | 2.07 | 60 |
| Example 9 | 0.16 (0.042–0.58) | 41 (37–47) | 256 | 2.21 | 120 |
| Lidocaine | 3.1 (1.5–6.6) | 18 (17–21) | 5.8 | 8.0 | 15 |
| Quinidine | 2.7 (2.0–3.7) | 48 (47–49) | 18 | 10.0 [1] | 15 |

TABLE 2

Effect on the total number of heart contractions in dogs, 24 hours after a two-step coronary ligature (Harris Model)

| Compound | dose in mmol/kg (mg/kg) | N | | base | 5 | 30 | 60 | 120 | 180 | 300 | 360 |
|---|---|---|---|---|---|---|---|---|---|---|---|
| Example 1 | 0.005 (1.76) | 4 | $\bar{x}$ s | 164 10.1 | 192 10.4 | 193 6.3 | 177 4.3 | 175 8.1 | 169 11.2 | — | — |
| Example 4 | 0.005 (1.93) | 4 | $\bar{x}$ s | 183 13 | 175 15 | 180 15.9 | 181 14.5 | 183 11.7 | — | — | — |
| Example 6 | 0.005 (2.07) | 5 | $\bar{x}$ s | 167 8.6 | 170 8.2 | 159 9.3 | 162 7.2 | 162 6.6 | — | — | — |
| Example 9 | 0.005 (2.21) | 3 | $\bar{x}$ s | 156 12.8 | 179 9.5 | 164 7.1 | 168 12.7 | 156 13.7 | 159 11.9 | 163 19.1 | 180 0.4 |
| Lidocaine | 0.02 (5.4) | 5 | $\bar{x}$ s | 146 7.3 | 139 6.7 | 138 3.8 | — | — | — | — | — |

TABLE 3

Effect on ectopic contractions in dogs, 24 hours after a two-step coronary ligature (Harris model)

| Compound | dose in mmol/kg (mg/kg) | N | | base | 5 | 30 | 60 | 120 | 180 | 300 | 360 |
|---|---|---|---|---|---|---|---|---|---|---|---|
| Example 1 | 0.005 (1.76) | 4 | $\bar{x}$ s | 99 0.75 | 30 18.1 | 47 16.6 | 54 15.7 | 68 3.4 | 80 5.5 | — | — |
| Example 2 | 0.005 (1.93) | 4 | $\bar{x}$ s | 88 5.3 | 26 16.9 | 24 6.5 | 75 7.2 | 90 2.3 | — | — | — |
| Example 6 | 0.005 (2.07) | 5 | $\bar{x}$ s | 78 7.5 | 20 10.1 | 4 3.1 | 37 14.9 | 76 6.6 | — | — | — |
| Example 9 | 0.005 (2.21) | 3 | $\bar{x}$ s | 90 2.0 | 21 5.7 | 38 15.0 | 42 23.3 | 42 14.1 | 73 9.7 | 79 4.9 | 89 2.3 |
| Lidocaine | 0.02 (5.4) | 5 | $\bar{x}$ s | 83 6.2 | 34 17.7 | 78 7.0 | — | — | — | — | — |

In Table 1

$ED_{50\ iv.}$ is the dose in mg/kg, which suppresses the fibrillatory effect of $CaCl_2$ in rats by 50% after i.v. administration of the substance. The data is analyzed by the Probit regression analysis with a confidence interval of $p=0.05$ (values in parentheses).

$LD_{50\ iv.}$ is lethal dose in mg/kg for 50% of the experimental animals of an orientating acute toxicity test on male or female Wistar rats of our own breed, iv. administration in the tail vein, 3–4 dosages, 10 animals per group. The data were analyzed by the Probit

EXAMPLE 1

5-(6-Dimethylamino-capronyl)-5,10-dihydro-11H-dibenzo(b,e)(1,4)-diazepine-11-one.HCl 5-(6-Bromocapronyl)-5,10-dihydro-11H-dipenzo(b,e)(1,4)-diazepine-11-one (7,75 g, 0.002 moles) is dissolved in 50 ml of dimethylformamide at room temperature and cooled to 2° C. and 10 ml of a solution of dimethylamine in dimethylformamide are added (72%, corresponding to 0.16 moles of dimethylamine). The whole is heated slowly, in a closed vessel, to room temperature and subsequently, for a half hour, at a bath temperature of 40° C. After that, a further 10 ml of dimethylamine solution are added and the procedure described above is repeated. Next, the dimethylformamide is distilled off under vacuum, the remaining oil is distributed between 30 ml of dilute ammonia solution and 50 ml of chloroform, the ammoniacal phase is shaken twice with 20 ml portions of chloroform, and the combined chloroform phases are extracted three times with 20 ml portions of 1:1 diluted hydrochloric acid.

The hydrochloric acid phases are made alkaline with about 10 ml of concentrated ammonia solution and extracted twice with 10 ml portions of chloroform and the combined chloroform phases are dried over sodium sulfate.

The sodium sulfate is removed by filtration and the chloroform is distilled off. The residue is treated with 40 ml of acetone and HCl is passed into the solution, until the pH reached a value of 1. The solution is subsequently evaporated, the residue is treated with 30 ml of ethyl acetate and 20 ml of acetone and, after 12 hours, the crystals formed are filtered off with suction and recrystallized from isopropanol.

The yield is 4.7 g (61% of the theoretical yield). The melting point is 183° C.

| Analysis for $C_{21}H_{26}N_3O_2Cl$: | calculated | found |
|---|---|---|
| C | 65.02% | 64.69% |
| H | 6.76% | 6.78% |
| N | 10.83% | 10.73% |
| Cl | 9.14% | 9.29% |

The starting material, 5-(6-bromocapronyl)-5,10-dihydro-11H-dibenzo(b,e)(1,4)-diazepine11-one, was synthesized as described below.

5,10-Dihydro-11H-dibenzo(b,e)(1,4)-diazepine-11-one (14.4 g, 0.07 moles) is dissolved in 100 ml of toluene, 18.8 g (0.088 moles) of bromocaproic acid chloride are slowly added dropwise and the reaction mixture is refluxed with stirring for 5 hours. Subsequently, 2 g of activated charcoal are added and the reaction mixture is refluxed for a further 15 minutes, filtered and allowed to crystallize. The crystaline material is filtered off with suction, washed with a small amount of toluene and, after drying, recrystallized from isopropanol.

The yield is 17.8 g (65.6% of the theoretical yield). The melting point is 138° to 139° C.

| Analysis for $C_{19}H_{19}BrN_2O_2$: | calculated | found |
|---|---|---|
| C | 58.92% | 59.08% |
| H | 4.94% | 4.94% |
| N | 7.23% | 7.24% |

EXAMPLE 2

5-(4-Diethylamino-butyryl)-5,10-dihydro-11H-dibenzo(b,e)(1,4)-diazepine-11-one 5-(4-Bromobutyryl)-5,10-dihydro-11H-dibenzo(b,e)(1,4)-diazepine-11-one (3.59 g, 0.01 moles) is dissolved in 25 ml of diethylamine and refluxed for 5 hours. Next, the excess diethylamine is distilled off and the residue is treated with 15 ml of water and 5 ml of aqueous ammonia solution and the reaction product is extracted with dichloroethane. The dichloroethane solution is shaken three times with 1:2 diluted hydrochloric acid and the hydrochloric acid phases are made alkaline with ammonia solution and extracted with dichloroethane. The dichloroethane is distilled off and the residue is crystallized from toluene.

The yield is 2.95 g (84% of the theoretical yield). The melting point is 166°-167° C.

| Analysis for $C_{21}H_{15}N_3O_2$: | calculated | found |
|---|---|---|
| C | 71.77% | 71.56% |
| H | 7.17% | 7.31% |
| N | 11.96% | 11.96% |

The 5-(4-bromobutyryl)-5,10-dihydro-11H-dibenzo(b,e)(1,4)-diazepine-11-one, starting material, was synthesized similarly to the starting material described in Example 1, from 5,10-dihydro-11H-dibenzo(b,e)(1,4)-diazepine-11-one and 4-bromobutyryl chloride. The yield is 74.3% of the theoretical yield and the melting point is 159°-161° C. (toluene).

| Analysis for $C_{17}H_{15}N_2O_2Br$: | calculated | found |
|---|---|---|
| C | 56.84% | 56.98% |
| H | 4.21% | 4.30% |
| N | 7.80% | 7.72% |
| Br | 22.24% | 22.02% |

EXAMPLE 3

5-(6-Diethylamino-capronyl)-5,10-dihydro-11H-dibenzo(b,e)(1,4)-diazepine-11-one 5-(6-Bromocapronyl)-5,10-dihydro-11H-dibenzo(b,e)(1,4)-diazepine-11-one (7.75 g, 0.02 moles) is refluxed in 50 ml of diethylamine for 5 hours. The reaction mixture is evaporated and the residue treated with 30 ml of water and 10 ml of concentrated ammonia solution. Subsequently, the aqueous phase is shaken three times with benzene. The combined benzene phases are extracted three times with 1:2 diluted hydrochloric acid and the acidic phase is made alkaline with concentrated ammonia solution. The oil, which precipitates, is shaken three times with benzene. The benzene is distilled off and the oily residue (7 g) is dissolved in 30 ml of toluene with heating. Upon cooling, a precipitate is formed, which is filtered off and washed with toluene and ether.

The yield is 5 g (65.9% of the theoretical yield). The melting point is 104°-105° C.

| Analysis for $C_{23}H_{29}N_3O_2$: | calculated | found |
|---|---|---|
| C | 72.79% | 72.63% |
| H | 7.70% | 7.68% |
| N | 11.07% | 11.20% |

For the synthesis of the 5-(6-diethylamino-capronyl)-5,10-dihydro-11H-dibenzo(b,e)(1,4)-diazepine-11-one hydrochloride salt, the aforementioned oily residue (7 g) is dissolved in 50 ml of hot isopropanol and HCl gas is passed into the solution, which has been cooled to room temperature, until the pH is 1. The reaction solution is then concentrated under vacuum to dryness. A further 50 ml of isopropanol are added and evaporated and the product is crystallized from 50 ml of acetonitrile with addition of activated charcoal.

The yield is 3.8 g (45.7% of the theoretical yield, based on 5-(6-bromocapronyl)-5,10-dihydro-11H-dibenzo(b,e)(1,4)-diazepine-11-one. The melting point is 179°–183° C.

| Analysis for $C_{23}H_{30}N_3O_2Cl$: | calculated | found |
|---|---|---|
| C | 66.41% | 66.23% |
| H | 7.27% | 6.99% |
| N | 10.10% | 10.18% |
| Cl | 8.52% | 8.43% |

EXAMPLE 4

8-Chloro-5-(4-diethylamino-butyryl)-5,10-dihydro-11H-dibenzo(b,e)(1,4)-diazepine-11-one 5-(4-Bromobutyryl)-8-chloro-5,10-dihydro-11H-benzo(b,e)(1,4)-diazepine-11-one (3.94 g, 0.01 moles) in 25 ml of diethylamine is refluxed with stirring for 5 hours. The excess of diethylamine is then distilled off and the residue treated with 15 ml of water and 5 ml of concentrated ammonia solution. The mixture is then extracted three times with chloroform and the combined chloroform phases are shaken three times with 1:2 diluted hydrochloric acid and made alkaline with concentrated ammonia solution. The precipitating oil is extracted three times with chloroform. Subsequently, the chloroform is distilled off and the residue is stirred with a little dry benzene, whereupon the crude product crystallizes. The product is recrystallized from toluene. The yield is 2.85 g (73.8% of the theoretical yield). The melting point is 163°–164° C.

| Analysis for $C_{21}H_{24}N_3O_2Cl$: | calculated | found |
|---|---|---|
| C | 65.36% | 65.53% |
| H | 6.27% | 6.41% |
| Cl | 9.19% | 9.01% |

The 5-(5-bromobutyryl)-8-chloro-5,10-dihydro-11H-dibenzo(b,e)(1,4)-diazepine-11-one, used as starting material, is synthesized similarly to the starting material described in Example 1 from 8-chloro-5,10-dihydro-11H-dibenzo(b,e)(1,4)-diazepine-11-one and 4-bromobutyryl chloride. The yield is 83.1% of the theoretical yield and the melting point is 176°–177° C.

| Analysis for $C_{17}H_{14}N_2O_2BrCl$: | calculated | found |
|---|---|---|
| C | 51.87% | 51.77% |
| H | 3.58% | 3.65% |

EXAMPLE 5

8-Chloro-5-(5-diethylamino-valeryl)-5,10-dihydro-11H-dibenzo(b,e)(1,4)-diazepine-11-one 5-(5-Bromovaleryl)-8-chloro-5,10-dihydro-11H-dibenzo(b,e)(1,4)-diazepine-11-one (4.07 g, 0.01 moles) in 25 ml of diethylamine is refluxed for 5 hours. The excess diethylamine is subsequently distilled off and 15 ml of water and 5 ml of concentrated ammonia solution are subsequently added to the residue. The ammoniacal phase is extracted with benzene and the benzene phase is shaken twice with 1:2 diluted hydrochloric acid, made alkaline with concentrated ammonia solution and extracted with benzene. The benzene is subsequently distilled off and the residue recrystallized from toluene.

The yield is 3.25 g (81.3% of the theoretical yield). The melting point is 159°–160° C.

| Analysis for $C_{22}H_{26}N_3O_2Cl$: | calculated | found |
|---|---|---|
| C | 66.07% | 66.00% |
| H | 6.55% | 6.63% |
| Cl | 8.86% | 8.65% |

The 5-(5-bromovaleryl)-8-chloro-5,10-dihydro-11H-dibenzo(b,e)(1,4)-diazepine-11-one, used as starting material, is synthesized similarly to the starting material described in Example 1, from 8-chloro-5,10-dihydro-11H-dibenzo(b,e)(1,4)-diazepine-11-one and 5-bromovaleryl chloride.

The yield is 180°–181° C. 87% of the theoretical. The melting point is

| Analysis for $C_{18}H_{16}N_2O_2BrCl$: | calculated | found |
|---|---|---|
| C | 53.03% | 53.26% |
| H | 3.96% | 4.02% |
| N | 6.87% | 7.14% |

EXAMPLE 6

8-Chloro-5-(6-diethylamino-capronyl)-5,10-dihydro-11H-dibenzo(b,e)(1,4)-diazepine-11-one 5-(6-Bromocapronyl)-8-chloro-5,10-dihydro-11H-dibenzo(b,e)(1,4)-diazepine-11-one (4.21 g, 0.01 moles) in 25 ml of diethylamine is refluxed for 5 hours. Subsequently, the excess diethylamine is distilled off, 15 ml of water and 5 ml of concentrated ammonia solution are added and the solution is extracted three times with benzene. The combined benzene phases are shaken three times with 1:2 diluted hydrochloric acid and the combined acidic phases made alkaline with concentrated ammonia solution. The precipitating oil is extracted three times with benzene. The benzene phase is washed with water and evaporated. The residue is recrystallized from a little toluene.

The yield is 2.65 g (64.1% of the theoretical yield). The melting point is 136°–138° C.

| Analysis for $C_{23}H_{28}N_3O_2Cl$: | calculated | found |
|---|---|---|
| C | 66.74% | 66.72% |
| H | 6.82% | 7.02% |
| N | 10.15% | 10.08% |
| Cl | 8.55% | 8.54% |

The 5-(6-bromocapronyl)-8-chloro-5,10-dihydro-11H-dibenzo(b,e)(1,4)-diazepine-11-one, used as starting material, is synthesized similarly to the starting material described in Example 1, from 8-chloro-5,10-dihydro-11H-dibenzo(b,e)(1,4)-diazepine-11-one and 6-bromocapronyl chloride.

The yield is 76.6% of the theoretical yield and the melting point is 170°–171° C. (toluene).

| Analysis for $C_{19}H_{18}N_2O_2BrCl$: | calculated | found |
|---|---|---|
| C | 54.11% | 54.01% |
| H | 4.30% | 4.26% |

EXAMPLE 7

8-Chloro-5-(7-diethylamino-enanthoyl)-5,10-dihydro-11H-dibenzo(b,e)(1,4)-diazepine-11-one 5-(7-Bromoenanthoyl)-8-chloro-5,10-dihydro-11H-dibenzo(b,e)(1,4)-diazepine-11-one in 25 ml of diethylamine is refluxed for 5 hours and the excess diethylamine is subsequently distilled off. The residue is treated with 15 ml of water and 5 ml of concentrated ammonia solution and extracted three times with benzene. The combined benzene phases are extracted three times with 1:2 diluted hydrochloric acid and the acidic phase is made alkaline with concentrated ammonia solution. Subsequently, the alkaline solution is extracted three times with benzene, the benzene is distilled off and the residue is dissolved in toluene with heating and allowed to crystallize. The crystalline material is filtered off with suction and washed consecutively with toluene and ether. The yield is 2.8 g (66.6% of the theoretical yield). The melting point is 145°–146° C.

| Analysis for $C_{24}H_{30}N_3O_2Cl$: | calculated | found |
|---|---|---|
| C | 67.35% | 67.30% |
| H | 7.06% | 7.08% |
| N | 9.81% | 9.77% |
| Cl | 8.22% | 8.17% |

The 5-(7-bromoenanthoyl)-8-chloro-5,10-dihydro-11H-dibenzo(b,e)(1,4)-diazepine-11-one, used as starting material, is synthesized similarly to the starting material described in Example 1, from 8-chloro-5,10-dihydro-11H-dibenzo(b,e)(1,4)-diazepine-11-one and 7-bromo-enanthoyl chloride.

The yield is 71.5% of the theoretical yield and the melting point is 159°–161° C. (toluene).

| Analysis for $C_{20}H_{20}N_2O_2BrCl$: | calculated | found |
|---|---|---|
| C | 55.13% | 55.02% |
| H | 4.63% | 4.68% |
| N | 6.43% | 6.40% |

EXAMPLE 8

8-Chloro-5-(6-N-morpholino-capronyl)-5,10-dihydro-11H-dibenzo(b,e)(1,4)-diazepine-11-one 5-(6-Bromocapronyl)-8-chloro-5,10-dihydro-11H-dibenzo(b,e)(1,4)-diazepine-11-one (5.6 g, 0.015 moles) and 5.23 g (0.06 moles) of morpholine are refluxed with stirring for 5 hours in 50 ml of toluene. After cooling, the desired product is extracted with 1:2 diluted hydrochloric acid from the toluene phase and the aqueous solution is made alkaline with concentrated ammonia solution and shaken with benzene. After the benzene phase is washed with water, the benzene is distilled off. The oily residue is dissolved in 120 ml of toluene with heating and allowed to cool. The precipitate is filtered off with suction, washed with toluene and then with ether and allowed to dry.

The yield is 3.7 g (59.6% of the theoretical yield). The melting point is 135°–136° C.

| Analysis for $C_{23}H_{26}N_3O_3Cl$: | calculated | found |
|---|---|---|
| C | 64.55% | 64.40% |
| H | 6.12% | 6.11% |
| N | 9.82% | 9.90% |
| Cl | 8.28% | 8.23% |

EXAMPLE 9

8-Chloro-5-(7-N-morpholino-enanthoyl)-5,10-dihydro-11H-dibenzo(b,e)(1,4)-diazepine-11-one 5-(7-Bromoenanthoyl)-8-chloro-5,10-dihydro-11H-dibenzo(b,e)(1,4)-diazepine-11-one (3.27 g, 0.0075 moles) and 2 g (0.0225 moles) of morpholine are refluxed with stirring in toluene for 5 hours. The reaction solution is cooled, extracted with 1:2 diluted hydrochloric acid and made alkaline with concentrated ammonia solution. The desired product is extracted three times with dichloroethane. The dichloroethane phase is washed with water and the dichloroethane is distilled off. The residue is recrystallized from 1:1 heptane-toluene. The crystalline material is filtered off with suction, washed with ether and dried.

The yield is 2 g (60.7% of the theoretical). The melting point is 102° C.–103° C.

| Analysis for $C_{24}H_{28}N_3O_3Cl$: | calculated | found |
|---|---|---|
| C | 65.22% | 65.31% |
| H | 6.39% | 6.32% |
| N | 9.51% | 9.40% |
| Cl | 8.02% | 7.77% |

EXAMPLE 10

8-Chloro-5,10-dihydro-5-/6-(4-methyl-piperazin-1-yl)capronyl/-11H-dibenzo(b,e)(1,4)-diazepine-11-one 5-(6-bromocapronyl-8-chloro-5,10-dihydro-11H-dibenzo(b,e)(1,4)-diazepine-11-one (8.44 g, 0.02 moles), 4.21 g (0.042 moles) of N-methylpiperazine and 50 ml of toluene are refluxed for 2 hours with stirring. The toluene solution is shaken subsequently with 20 ml of water. The toluene phase is extracted twice with 10 ml of 1:1 diluted hydrochloric acid, the combined acidic phases are made alkaline with concentrated ammonia solution and shaken once with 30 ml of chloroform and twice with 10 ml of chloroform and the combined chloroform phases are evaporated. The residue is treated twice with 50 ml of isopropanol and evaporated each time. Subsequently, 10 ml of toluene are added, the temperature is raised slightly and the crystalline material is filtered off with suction.

The yield is 6 g (68% of the theoretical yield). The melting point is 142° C.–147° C.

| Analysis for $C_{24}H_{29}N_4O_2Cl$: | calculated | found |
|---|---|---|
| C | 65.37% | 65.47% |
| H | 6.68% | 6.67% |
| N | 12.71% | 12.31% |
| Cl | 8.04% | 7.98%5 |

EXAMPLE 11

5,10-Dihydro-/6-(4-methyl-piperazin-1-yl)-capronyl/-11H-dibenzo(b,e)(1,4)-diazepine-11-one 5-(6-Bromocapronyl)-5,10-dihydro-11H-dibenzo(b,e)(1,4)-diazepine-11-one (5.8 g, 0.015 moles), 3.2 g (0.032 moles) of N-methylpiperazine and 40 ml of toluene are refluxed with stirring for 4 hours. Subsequently, the reaction solution is evaporated under vacuum and the residue is treated with 50 ml of chloroform. The chloroform phase is shaken twice with 20 ml of 1:1 diluted hydrochloric acid, the combined acidic phases are treated with 20 ml of chloroform, made alkaline with concentrated ammonia solution, and shaken with chloroform. The chloroform phase is removed. The ammoniacal phase is shaken twice with 20 ml of chloroform and the combined chloroform phases are dried over sodium sulfate and evaporated. The oily residue is boiled up with 20 ml of isopropanol, the isopropanol is evaporated and the residue is crystallized from 20 ml of hot toluene.

The yield is 4.7 g (77% of the theoretical yield). The melting point is 129° C. (decomposition).

| Analysis for $C_{24}H_{30}N_4O_2$: | calculated | found |
| --- | --- | --- |
| C | 70.91% | 70.52% |
| H | 7.44% | 7.37% |
| N | 13.78% | 13.46% |

EXAMPLE 12

8-Chloro-5-(6-ethylamino-capronyl)-5,10-dihydro-11H-dibenzo(b,e)(1,4)-diazepine-11-one.HCl 5-(6-Bromocapronyl)-8-chloro-5,10-dihydro-11H-dibenzo(b,e)(1,4)-diazepine-11-one (8.44 g, 0.02 moles) is dissolved in 50 ml of dimethylformamide, treated at 2° C. with 10 ml of ethylamine solution (0.17 moles, approx. 75% in dimethylformamide), heated for 0.5 hours in a closed vessel to 50° C., treated once again at 2° C. with 5 ml of the above ethylamine solution, heated once more for 0.5 hours at 50° C. in a closed vessel, stirred with 10% activated charcoal at an elevated temperature and evaporated to dryness under vacuum.

The residue is treated with 50 ml of chloroform, evaporated to dryness, taken up in 50 ml of isopropanol, if necessary with the addition of 20 to 40% of water and acidified fied to a pH of 1 by passing in HCl gas.

The acidic solution is evaporated to dryness under vacuum, treated once again with isopropanol, once more evaporated to dryness and recrystallized from isopropanol using activated charcoal.

At this stage, the Mettler melting point is 187° C.-191° C. The product is boiled out again with 30 ml of acetonitrile.

The yield is 3.0 g (35.4% of the theoretical yield). The melting point is 190° C.-195° C. (decomposition).

| Analysis for $C_{21}H_{25}N_3O_2Cl_2$: | calculated | found |
| --- | --- | --- |
| C | 59.72% | 59.40% |
| H | 5.97% | 5.94% |
| N | 9.95% | 9.96% |
| Cl | 16.79% | 16.97% |

EXAMPLE 13

5-(6-Ethylamino-capronyl)-5,10-dihydro-11H-dibenzo(b,e)(1,4)-diazepine-11-one.HCl 5-(6-Bromocapronyl)-5,10-dihydro-11H-dibenzo(b,e)(1,4)-diazepine-11-one (7.8 g, 0.02 moles) is dissolved in 50 ml of dimethylformamide, treated at 2° C. with 10 ml of ethylamine solution (0.17 moles, approx. 75% in dimethylformamide) heated for 0.5 hours at 50° C. in a closed vessel, treated once again at 2° C. with 10 ml of the above ethylamine solution and left for 1 hour at 50° C.

The reaction solution is subsequently stirred in the cold with 10% (based on the product used) of activated charcoal and evaporated to dryness under vacuum. The residue is dissolved in 30 ml of chloroform and shaken twice with 20 ml of 1:1 diluted hydrochloric acid. The acidic phases are combined, 20 ml of chloroform is added to them and they are made alkaline with concentrated ammonia solution. The two phases are shaken and the chloroform phase is removed. The ammoniacal phase is shaken twice more with 20 ml of chloroform and the combined chloroform phases are dried over sodium sulfate, a little activated charcoal being added. After filtration, the chloroform phase is evaporated. The oily residue is treated with 20 ml of isopropanol and 6 ml of water. Hydrogen chloride gas is passed in until the pH reaches a value of 1. The solution is evaporated to dryness under vacuum. Once again, 50 ml of isopropanol are added and the solution is evaporated to dryness. The residue is boiled out with 25 ml of acetonitrile.

The yield is 5.1 g (65.4% of the theoretical yield). The melting point is 189.5° C.-196.5° C. (decomposition).

| Analysis for $C_{21}H_{26}N_3O_2Cl$: | calculated | found |
| --- | --- | --- |
| C | 65.02% | 65.23% |
| H | 6.76% | 6.54% |
| N | 10.83% | 10.89% |
| Cl | 9.14% | 8.91% |

EXAMPLE 14

5-(6-Diisopropylamino-capronyl)-5,10-dihydro-11H-dibenzo(b,e)(1,4)-diazepine-11-one 5-(6-Bromocapronyl)-5,10-dihydro-11H-dibenzo(b,e)(1,4)-diazepine-11-one (5.8 g, 0.015 moles) is refluxed for 21 hours with 20 ml of diisopropylamine. The reaction mixture is evaporated and the residue is taken up in 50 ml of chloroform, extracted twice with 1:1 diluted ammonia solution and subsequently twice with 20 ml and once with 10 ml of concentrated hydrochloric acid. The combined acidic phases are shaken with 20 ml of chloroform, made strongly alkaline with concentrated ammonia solution and extracted three times with 30 ml of chloroform. The combined chloroform phases are shaken twice with 20 ml of water and evaporated to dryness. The residue is dissolved in hot toluene and crystallizes out on prolonged standing.

The yield is 1.7 g (25.6% of the theoretical yield). The melting point is 100° C.-106° C. (decomposition).

| Analysis for $C_{25}H_{32}N_3O_2$: | calculated | found |
| --- | --- | --- |
| C | 73.68% | 73.66% |
| H | 8.16% | 7.93% |
| N | 10.31% | 10.40% |

EXAMPLE 15

5-(6-Diethylamino-capronyl)-5,10-dihydro-11H-dibenzo(b,e)(1,4)-diazepine-11-one 5-(6-Chlorocapronyl)-5,10-dihydro-11H-dibenzo(b,e)(1,4)-diazepine-11-one (10 g, 0.029 moles) is dissolved in 100 ml of dimethylformamide, treated with 50 ml (0.48 moles) of diethylamine and stirred for 33 hours at a bath temperature of 65° C. The reaction mixture is subsequently evaporated to dryness. The residue is distributed at an elevated temperature between 120 ml of toluene, 70 ml of water and 40 ml of concentrated ammonia solution. The toluene phase is removed and the aqueous phase is shaken twice more with 50 ml of toluene. The combined toluene phases are extracted three times with 50 ml of 1:1 diluted hydrochloric acid.

The combined acidic phases are made strongly alkaline with ammonia solution and shaken three times with 50 ml of toluene. The combined toluene phases are extracted twice with 50 ml of water.

The toluene phases are evaporated under vacuum and once more treated with 50 ml of toluene and evaporated. The residue is recrystallized twice from toluene with the addition of activated charcoal. For the crystallization of the compound, 10 ml of cyclohexane are added.

The yield is 3.1 g (27.2% of the theoretical yield). The melting point is 98° C. to 100° C.

| Analysis for $C_{23}H_{29}N_3O_2$: | calculated | found |
|---|---|---|
| C | 72.79% | 72.62% |
| H | 7.70% | 7.62% |
| N | 11.07% | 11.08% |

EXAMPLE 16

8-Chloro-5-(6-cyclohexylamino-capronyl)-5,10-dihydro-11H-dibenzo(b,e)(1,4)-diazepine-11-one 5-(6-Bromocapronyl)-8-chloro-5,10-dihydro-11H-dibenzo(b,e)(1,4)-diazepine-11-one and 4.0 g (0.04 moles) of cyclohexylamine are refluxed for 5 hours in 50 ml of toluene. Subsequently, the reaction mixture is treated with 25 ml of toluene and 50 ml of water and stirred until the oily layer, which is formed during the reaction, has dissolved completely. The aqueous phase is removed and the toluene phase is shaken three times with water and then evaporated to dryness. The residue is dissolved in 90 ml of acetone and filtered. The acetone solution is then treated with 3 ml of concentrated hydrochloric acid. The precipitated oil is dissolved by stirring. After some time, crystalline material is deposited from the solution; it is recrystalized from absolute ethanol.

The yield is 6.3 g (64.9% of the theoretical yield). The melting point is 174° C.–175° C.

| Analysis for $C_{25}H_{32}N_3O_{2.5}Cl_2$: | calculated | found |
|---|---|---|
| C | 61.85% | 61.56% |
| H | 6.64% | 6.57% |
| N | 8.65% | 8.66% |
| Cl | 14.61% | 14.67% |

EXAMPLE 17

5-(6-cyclohexylamino-capronyl)-5,10-dihydro-11H-dibenzo(b,e)(1,4)-diazepine-11-one 5-(6-Bromocapronyl)-5,10-dihydro-11H-dibenzo(b,e)(1,4)-diazepine-11-one and 2.5 g (0.025 moles) of cyclohexylamine are refluxed in 25 ml of toluene for 5 hours. Subsequently, 2.3 ml of hydrobromic acid (48%) and 20 ml of water are added. The lower layer is separated from the upper layer, treated with 30 ml of acetone and refluxed for 15 minutes. The residue is filtered, washed with water and treated with 50 ml of acetone. The suspension obtained is refluxed for 1 hour and the residue is filtered and washed with a little acetone. After drying, the yield is 2.6 g (52.5% of the theoretical yield) and the melting point is 250° C.–251° C.

| Analysis for $C_{25}H_{33}N_3O_{2.5}Br$: | calculated | found |
|---|---|---|
| C | 60.61% | 60.92% |
| H | 6.71 | 6.63% |
| N | 8.48% | 8.65% |
| Br | 16.43% | 16.00% |

We claim:

1. The compounds:
5-(6-ethylamino-capronyl)-5,10-dihydro-11H-dibenzo(b,e)(1,4)-diazepine-11-one
8-chloro-5-(6-ethylamino-capronyl)-5,10-dihydro-11H-dibenzo(b,e)(1,4)-diazepine-11-one
5-(6-isopropylamino-capronyl)-5,10-dihydro-11H-dibenzo(b,e)(1,4)-diazepine-11-one
8-chloro-5-(6-isopropylamino-capronyl)-5,10-dihydro-11H-dibenz(b,e)(1,4)-diazepine-11-one
5-(6-cyclohexylamino-capronyl)-5,10-dihydro-11H-dibenzo(b,e)(1,4)-diazepine-11-one
8-chloro-5-(6-cyclohexylamino-capronyl)-5,10-dihydro-11H-dibenz(b,e)(1,4)-diazepine-11-one
and their pharmaceutically acceptable acid addition salts.

2. A process for treating arrhythmia, and bradyarrhythmia, which comprises administering to a host in need therefor a 5-(ω-aminoacyl)-5,10-dihydro-11H-dibenzo(b,e)(1,4)-diazepine-11-ones of formula (I)

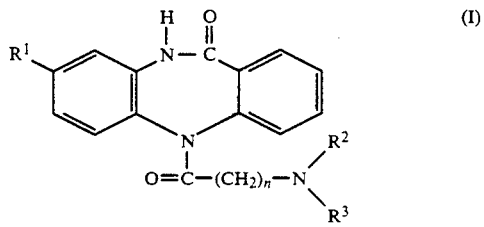

wherein
$R^1$ is hydrogen or chlorine,
$R^2$ and $R^3$ can be the same or different and are hydrogen, a $C_{1-3}$ alkyl residue or, together with the nitrogen atom to which they are linked, a morpholino, or N-methylpiperazino group, and
n is a cardinal number from 3 to 6,
provided that, when $R^2$ is hydrogen, $R^3$ can also be cyclohexyl, and pharmaceutically acceptable acid addition salts thereof.

3. The process of claim 2, wherein said 5-(ω-aminoacyl)-5,10-dihydro-11H-dibenzo[b,e][1,4]-diazepine-11-one is:
5-(6-dimethylamino-capronyl)-5,10-dihydro-11H-dibenzo[b,e][1,4]-diazepine-11-one;
5-(4-diethylamino-butyl)-5,10-dihydro-11H-dibenzo[b,e][1,4]-diazepine-11-one;
5-(6-diethylamino-capronyl)-5,10-dihydro-11H-dibenzo[b,e][1,4]-diazepin-11-one;
8-chloro-5-(4-diethylamino-butyryl)-5,10-dihydro-11H-dibenzo[b,e][1,4]-diazepine-11-one;
8-chloro-5-(5-diethylamino-valeryl)-5,10-dihydro-11H-dibenzo[b,e][1,4]-diazepine-11-one;

8-chloro-5-(6-diethylamino-capronyl)-5,10-dihydro-11H-dibenzo[b,e][1,4]-diazepine-11-one;

8-chloro-5-(7-diethylamino-enanthoyl)-5,10-dihydro-11H-dibenzo(b,e)(1,4)-diazepine-11-one;

8-chloro-5-(6-N-morpholino-capronyl)-5,10-dihydro-11H-dibenzo(b,e)(1,4)-diazepine-11-one;

8-chloro-5-(7-N-morpholino-enanthoyl)-5,10-dihydro-11H-dibenz(b,e)(1,4)-diazepine-11-one;

8-chloro-5,10-dihydro-5-/6-(4-methyl-piperazin-1-yl)-capronyl/-11H-dibenzo[b,e][1,4]-diazepine-11-one;

5,10-dihydro-5-[6-(4-methyl-piperazin-1-yl)-capronyl]-11H-dibenz[b,e][1,4]-diazepine-11-one;

5-(6-diisopropylamino-capronyl)-5,10-dihydro-11H-dibenzo[b,e][1,4]-diazepine-11-one;

5-(6-ethylamino-capronyl)-5,10-dihydro-11H-dibenzo[b,e][1,4]-diazepine-11-one;

8-chloro-5-(6-ethylamino-capronyl)-5,10-dihydro-11H-dibenzo[b,e][1,4]-diazepine-11-one;

5-(6-isopropylamino-capronyl)-5,10-dihydro-11H-dibenzo[b,e][1,4]-diazepine-11-one;

8-chloro-5-(6-isopropylamino-capronyl)-5,10-dihydro-11H-dibenzo[b,e][1,4]-diazepine-11-one;

5-(6-cyclohexylamino-capronyl)-5,10-dihydro-11H-dibenzo[b,e][1,4]-diazepine-11-one; or 8-chloro-5-(6-cyclohexylamino-capronyl)-5,10-dihydro-11H-dibenz[b,e][1,4]-diazepine-11-one; or their pharmaceutically acceptable acid addition salts.

* * * * *